United States Patent [19]

Hadwiger

[11] Patent Number: 5,104,437

[45] Date of Patent: * Apr. 14, 1992

[54] METHOD FOR TREATING CEREAL CROP SEED WITH CHITOSAN TO ENHANCE YIELD ROOT GROWTH, AND STEM STRENGTH

[75] Inventor: Lee A. Hadwiger, Pullman, Wash.

[73] Assignee: Washington State University Research Foundation, Pullman, Wash.

[*] Notice: The portion of the term of this patent subsequent to Dec. 12, 2006 has been disclaimed.

[21] Appl. No.: 606,459

[22] Filed: Oct. 31, 1990

Related U.S. Application Data

[60] Division of Ser. No. 344,287, Apr. 4, 1989, Pat. No. 4,978,381, which is a continuation-in-part of Ser. No. 795,702, Nov. 5, 1985, abandoned, which is a continuation of Ser. No. 658,084, Oct. 5, 1984, abandoned.

[51] Int. Cl.$^5$ .................... A01N 43/16; C08B 37/08
[52] U.S. Cl. .......................................... 71/77; 71/88; 47/57.6; 514/55; 536/20
[58] Field of Search ................ 71/77, 88; 514/55; 536/20

[56] References Cited

U.S. PATENT DOCUMENTS 4,886,541 12/1989 Hadwiger ............................. 71/77
4,978,381 12/1990 Hadwiger ............................. 71/77

OTHER PUBLICATIONS

Takemoto, Kiichi "Chemistry and Use of Chitin and Chitosan", *Gendai Kagaku*, 1981 p. 57-61.
C. R. Allan and L. A. Hadwiger, "The Fungicidal Effect of Chitosan on Fungi of Varying Cell Wall Composition", *Experimental Mycology*, vol. 3, pp. 285-287 (1979)..

Primary Examiner—Richard L. Raymond
Assistant Examiner—S. Mark Clardy
Attorney, Agent, or Firm—Wegner, Cantor, Mueller & Player

[57] ABSTRACT

Commercially produced chitosan applied to cereal crop seeds at rates of 60 μg to 1000 μg per gram of seed enhances root development, crown diameter, mature straw strength and crop yield. Dry chitosan, when dissolved in dilute acid and neutralized, is applied directly to cereal crop seed with only minor modification to seed treating machinery and methods. In addition to a clear benefit in cereal crop yield, the chitosan treated seed can be planted early to reduce erosion and it can be planted in regions having soil infested with root rotting organisms and not suffer extensive lodging that would prevent seed recovery by commercial harvesters.

19 Claims, No Drawings

METHOD FOR TREATING CEREAL CROP SEED WITH CHITOSAN TO ENHANCE YIELD ROOT GROWTH, AND STEM STRENGTH

This application is a divisional of co-pending application Ser. No. 344,287, filed Apr. 4, 1989, now U.S. Pat. No. 4,978,381, which, in turn, is a continuation-in-part of application Ser. No. 795,702, filed Nov. 5, 1985, now abandoned, which was a continuation of Ser. No. 658,084, filed Oct. 5, 1984, and now abandoned.

FIELD OF THE INVENTION

This invention pertains to mthods for treating the seed of cereal crops, which are defined as members of the grass family (Graminae) that produce edible, starchy grains and are characterized by long, narrow blades. Wheat, barley, oats, rye, and rice are cereal crops.

BACKGROUND OF THE INVENTION

One of the major problems in growing ceral crops is the lodging (falling over) of plants prior to harvest, which prevents the mechanical recovery at harvest of high yielding plant heads. Researchers have tried alleviate this problem by:
1. Breeding stiffer stemmed varieties:
2. Using chemical treatments such as benzamidazoletype fungicides (Benlate) to reduce root rot;
3. Recommending that planting dates for winter crops be delayed so that organisms have minimal time to initiate the root rotting process prior to the slow growth phase of winter; and
4. Recommending no-till or minimum tillage procedures that leave crop debris to reduce the erosion that is rampant when planting dates are delayed.

Each of these alternative procedures are partial solutions to yield losses. However, each has serious drawbacks.

It has been impossible to breed for straw strength and still retain all of the other desirable agronomic traits, e.g., winter hardiness, milling quality yield, disease resistance, etc., at the same time because the high yielding heads place unusually severe strain on the plant stem.

Lodging has been reduced by fungicides that are derivatives of methYl 1-(butylcarbamoyl)-2-benzimidazole carbamate (Benlate), which reduce the incidence of root rotting and thus retain original straw strength. Extended use of this chemical, however, has resulted in the selection of fungal pathogens that are resistant to its fungicidal effect and, thus, effectiveness is greatly diminished. Only emergency Food and Drug Administration clearance has been obtained in the United States of America for use of this chemical on wheat because of potential side effects. Finally, its cost of treatment is very high.

Delaying the planting date has reduced lodging; however, it prevents the time dependent development of large seedling plants needed for ground cover prior to the onset of winter rains and erratic snow melts that erode away large tonnages of soil each year. The latter problem can be reduced by minimal tillage practices that leave straw on top of the soil at planting time. However, minimal tillage, which produces generally lower yields, leaves weeds untilled as well and must be accompanied by additional herbicide and pesticide treatments requiring expensive machinery for application.

Accordingly, a need exists for a method that will increase the straw strength and the root development of cereal crops at a commercially feasible cost while still maintaining or increasing the amount of yield.

SUMMARY OF THE INVENTION

This invention comprises a novel chitosan seed treatment that strengthens the stems of cereal crop plants, such as wheat, oats, barley, rye, and rice, helping to preserve their water-carrying capacity, greatly reducing lodging (plants falling over before harvest), and increasing yield. The lodging problem is most severe for winter crops when seed is planted early so that the plants can cover the ground prior to the soil eroding winter rains. Thus, by using this seed treatment, farmers will be able to plant crops early and reduce the erosion loss that exceeds 9071.8 kilograms per 0.4047 hectare in some parts of the United State of America.

While this invention is applicable to any of the cereal crops, primary work has been done with wheat, barley, and oats and this specification will discuss the invention using these cereal grains as an embodiment.

The problem of lodging of high yielding cereal plants can be rectified by seed treatment with the naturally occurring carbohydrate, chitosan. Commercially produced chitosan when applied in an aqueous form to cereal seeds is able, under field conditions, to greatly increase the development of the plant's root system, to substantially increase the diameter of the stem, and, in association with these specific and other intangible morphological and biochemical developments, to enhance yield. The chitosan treatment results in a plant that is beneficial to erosion control, resistant to lodging, and superior in yield over non-treated plants. The method of treatment comprises the direct application of chitosan derived from various shell sources, such as crab, lobster, shrimp and other marine life, in a nearly neutral aqueous solution to wheat seeds prior to planting.

Accordingly, it is a primary object of the present invention to provide a method for increasing the straw strength and root development of cereal crops while increasing the amount of yield.

This and further objects and advantages will be apparent to those skilled in the art in connection with the detailed description of the preferred embodiments set forth below.

DETAILED DESCRIPTION OF THE PREFERRED EMBODIMENTS

Chitosan is a polymer made up of a hexosamine sugar (glucosamine) whose molecules are linked (1, 4) into chains that can exceed molecular weights of one million. Chitosan compounds in a range of up to and exceeding $1 \times 10^6$ molecular weight are derived commerically from chitin. Chitin, an amino cellulose derivite, is the second most abundant polymer occurring in nature, existing, for example, in the cell walls of fungi, bovine cartilage, and the hard shells of insects and crustaceans. Wastes from the shrimp, lobster, and crab seafood industries contain 10-30% chitin. Chitosan is produced by deacetylating chitin This invention is effective if the deacetylation exceeds about 90% and it is most effective when approaching 100% deacetylation.

Dry chitosan as either flakes, granules, or powder is suitable as a starting material. The more finely dispersed the chitosan, the more quickly it can be dissolved in a dilute aqueous acid (e.g., 1% acetic acid or dilute hydrochloric acid, sulfuric acid, or formic acid).

Typically, a quantity of chitosan suitable for planting a 64.75 hectare field (quarter section) of wheat would be mixed as follows 1.089 kilograms of crab shell chitosan is dissolved in 30.28 liters of 1% acetic acid. 48 hours is allowed at room temperature for the chitosan to dissolve with stirring. $H_2O$ is then added to bring the volume to 98.42 liters or until the viscosity is reduced enough to feed through the dispenser of commercial seed treating machinery. (Most seed treatment machines utilized to handle water based seed treatments can be utilized with the aqueous solution of chitosan.) The solution is neutralized to pH 6.0 to 6.5 with 0.757 to 0.871 liters of 6.0 N NaOH. NaOH is added slowly with stirring, because localized changes to a pH higher than 7.0 will cause the chitosan to precipitate. Once near neutrality, the viscosity of the opaque aqueous preparation of chitosan is reduced to the designed viscosity with $H_2O$ to approximately 98.42 liters. From this, approximately 0.473 liters is added to each bushel (27.22 kg.) of wheat seed. This volume of aqueous chitosan increases the moisture percentage of 27.22 kilograms of wheat seed by 1.6%.

Chitosan seed treatments were found to be effective using rates ranging from 60 $\mu$g chitosan per gram of wheat seed to 1000 $\mu$g chitosan per gram of wheat seed. Optimal results were obtained at 250 $\mu$g chitosan per gram of wheat seed. This rate is 0.00635 kilogram chitosan per 27.22 kilograms (1 bushel) of wheat seed. 27.22 kilograms per 0.4047 hectare is the average seeding rate for wheat in most areas.

For barley, optional results are obtained at about 60 $\mu$g per gram of barley seed. For oats, such results are obtained in the range 475 $\mu$g to 525 $\mu$g per gram of oat seed.

The native chitosan required to treat seed prior to planting is inexpensive. For winter wheat, chitosan treated wheat seed can be planted in late summer or as early as August as moisture is available. The chitosan treatment enhances stem diameter by approximately 10%. Although chitosan-treated plants grown in soils heavily infested with root rotting disease are susceptible to development of some rotting symptoms such as stem discoloration and white heads, the larger stem diameter and the extensive root system caused by the treatment maintain greater stem strength and an adequate water transporting capacity of stem vascular systems. As a result of seed treatment with this naturally occurring compound, 10-30% higher yields are obtained at a low cost, soil erosion is minimized, and the chitosan is readily degraded to simple amino sugar residues and/or metabolized by soil organisms.

Plants and micro-organisms contain chitosanase and other degradative enzymes with the potential to digest chitosan into smaller fragments and eventually into hexosamines that can be utilized as nutrients by soil microflora.

If seed is treated in a humid environment, a posttreatment drying step must be added to reduce the moisture content of the treated grain to the 10-14% range in order to prevent premature germination of the seed; therefore, the more viscous the chitosan preparation, the less drying that will be required. Highly viscous chitosan preparations can be mixed with seed using any machinery marketed for cement mixing. Modifications of grain augering devices will also enable chitosan to be added to seed as it is being loaded aboard trucks just prior to transport to the field for planting. This eliminates the need for extensive dryign to prevent seed germination.

Chitosan seed applications are not detrimentally influenced by fertilizer supplements, herbicide applications or irrigation programs. Other commercial seed treatments, e.g., insecticides and fungicides, should be applied prior to chitosan. Components already on the seed will be attached to the seed by the chitosan, which leaves a "cellophane-like" surface on seed after drying. The chitosan-treated seed can be planted directly in any commercial planter. Special planters that automatically administer fertilizers, soil sterilants, herbicides, etc. can be utilized to treat seeds with chitosan as they are being planted. Chitosan labelled with tritium, [$^3$H]-Chitosan, added to seeds was translocated to the developing plant indicating that a large portion of the chemical is distributed systemically.

Dry chitosan can be stored indefinitely at room temperature without loss of biological activity. Chitosan can be mixed as described above at room temperature. Chitosan has no known toxicity and can be supplemental to the diet of animals without detrimental side effects. The physical irritation properties of chitosan have not been investigated in long term studies, however, and, therefore, the same basic precautions taken in the handling of other fibrous materials or powders, e.g., cotton fibers or flour, may apply to chitosan.

The root enhancing, stem diameter increasing, and strengthening effect of chitosan seed treatment is seen at both early and late seeding dates for winter crops; however, the major beneficial effects for erosion reduction are obtained with early seeding dates. This allows the development of the large seedling plants needed for ground cover prior to the onset of winter rains and snow melts while the chitosan minimizes the problem of root rotting.

The following data illustrate examples of enhanced properties obtained in wheat, oats, and barley through the use of this invention.

EXAMPLE 1

Enhanced Seedling Development

Seedlings from chitosan treated Daws wheat seeds (200 $\mu$g chitosan/g seed) 4 months after planting at Washtuchna, Washington under circle irrigation, Oct. 15, 1983.

| Seed Treatment | Ave. diameter of crown (lower stem) mm | Ave. length of stem from crown to first leaf cm | Ave. wt. root system per 30 plants | |
|---|---|---|---|---|
| | | | fresh wt g | dry wt g |
| $H_2O$ control | 2.3 | 3.7 | 1.002 | .139 |
| Chitosan (200 $\mu$g/g seed) | 3.7 | 3.8 | 2.690 | .330 |

EXAMPLE 2

Reduced Lodging

Daws winter wheat 1983 crop lodging reading on outside row of 4'×100' plot.

| Treatment g chitosan/gram seed | Stems lodged no. |
|---|---|
| Chitosan 62 | 275 |

-continued

| Treatment g chitosan/gram seed | Stems lodged no. |
|---|---|
| Control | 468 |
| Chitosan 125 | 313 |
| Control | 948 |
| Chitosan 250 | 143 |
| Control | 835 |
| Chitosan 500 | 186 |
| Control | 652 |
| Chitosan 1000 | 250 |
| Control | 410 |

EXAMPLE 3

Increased Stem Diameter

Effect of chitosan seed treatment on stem diameter of Daws wheat at maturity—1983.

| Chitosan applied per gram seed g | Stem diameter mm | % increase |
|---|---|---|
| Chitosan 62 | 3.872[a] | — |
| Control | 3.239 | 19 |
| Chitosan 125 | 3.432 | — |
| Control | 3.231 | 6 |
| Chitosan 250 | 3.606 | — |
| Control | 3.322 | 9 |
| Chitosan 500 | 3.997 | — |
| Control | 3.651 | 9 |

[a]Average diameter of 100 stems.

EXAMPLE 4

Enhanced Yield

Effect of Chitosan Seed Treatment on Daws Winter Wheat Yield in 1983

| | Application kg/bushel (27.2 kg) seed | Avg. yield kh/hectare | % Increase Over Control |
|---|---|---|---|
| Chitosan 1000 µg/g | .0268 | 6066.0[a] | 14% |
| Control | | 5299.3 | |
| Chitosan 500 µg/g | .0132 | 6032.3 | 13% |
| Control | | 5232.1 | |
| Chitosan 250 µg/g | .0064 | 6341.7 | 21% |
| Control | | 5662.5 | |
| Chitosan 125 µg/g | .0032 | 6153.4 | 8% |

[a]Yield was an average of four replications. Plot size was 1.22 m × 9.14 m. Lodging in control plots was up to 60%. Yield included lodged wheat recovered by hand at harvest.

EXAMPLE 5

Enhanced Yield

| Fielder spring wheat treatment - 1982 yield | |
|---|---|
| | % of control |
| Chitosan (320 µg/g) seed treatment only | 131 |
| Control | 100 |

EXAMPLE 6

Enhanced Yield

| Daws winter wheat treatment - 1982 yield | |
|---|---|
| | % of control |
| Chitosan (500 µg/g) seed treatment | 107 |
| Control | 100 |

EXAMPLE 7

Enhanced Disease Resistance

Effects of Chitosan Seed Treatment Daws Wheat Pseudocercosporella herpotrichoides Disease symptoms on Wheat Straw at Harvest

| Symptom Value | No. of Straws/Sympton Value Category (Chitosan treatment and control) | | | | |
|---|---|---|---|---|---|
| | 0 | 1 | 2 | 3 | 4 |
| 62 µg/g | 4 | 22 | 35 | 22 | 17 |
| Control | 8 | 28 | 40 | 24 | 8 |
| 125 µg/g | 5 | 13 | 24 | 12 | 46 |
| Control | 1 | 8 | 21 | 49 | 21 |
| 250 µg/g | 2 | 15 | 19 | 48 | 18 |
| Control | 0 | 8 | 39 | 48 | 5 |
| 500 µg/g | 7 | 19 | 37 | 21 | 16 |
| Control | 0 | 4 | 35 | 59 | 7 |
| 1000 µg/g | 0 | 8 | 32 | 55 | 5 |
| Control | 1 | 9 | 38 | 48 | 4 |

Mature Stem Symptom Values
Clean Straw = 0
Slight Discoloration = 1
Scattered Lesions = 2
Coalescing Lesions = 3
Diseased & Broekn = 4

EXAMPLE 8

Enhanced Yield

KAMIAK BARLEY
WINTER GROWN
Whitlow Farm, Pullman, Washington

| TREATMENT | kg/hectare | % OF CONTROL |
|---|---|---|
| Control[a] | 8135.20 | — |
| 1000 µg/g seed[b] | 7568.77 | 93 |
| 500 µg/g seed[b] | 8301.23 | 102 |
| 250 µg/g seed[b] | 8276.79 | 101 |
| 125 µg/g seed[b] | 8960.43 | 110 |
| 62 µg/g seed[b] | 10010.31 | 123 |

[a]Average of 10 plots (generally 1.22 m × 9.14 m); chitosan was applied with water - an equivalent amount of water without the chitosan was applied to the control plots.
[b]Average of 2 plots (generally 1.22 m × 9.14 m).

EXAMPLE 9

Enhanced Yield

CORRET OATS
SPRING PLANTED
Plant Pathology Farm, Pullman, Washington

| TREATMENT | kg/hectare | % OF CONTROL |
|---|---|---|
| Control[a] | 2485.46 | — |
| 1000 µg/g seed[b] | 2734.57 | 110 |
| 500 µg/g seed[b] | 3344.90 | 135 |
| 250 µg/g seed[b] | 2758.95 | 111 |
| 125 µg/g seed[b] | 2392.72 | 96 |

-continued

CORRET OATS
SPRING PLANTED
Plant Pathology Farm, Pullman, Washington

| TREATMENT | kg/hectare | % OF CONTROL |
|---|---|---|
| 62 μg/g seed[b] | 2148.56 | 86 |

[a]Average of 10 plots (generally 1.22 m × 9.14 m); chitosan was applied with water - an equivalent amount of water without the chitosan was applied to the control plots.
[b]Average of 2 plots (generally 1.22 m × 9.14 m).

EXAMPLE 10

Wheat Seedling Weights

Variety: VONA
Date harvested: 18 December 1985
Location: Alva, Oklahoma

| | mean wt per stem (g) | | mean wt per root (g) | |
|---|---|---|---|---|
| | fresh | dry | fresh | dry |
| Group I | | | | |
| Control | 2.01 | 0.38 | 1.98 | 0.04 |
| Chitosan solution 0.473 liter | 3.13 | 0.47 | 2.87 | 0.01 |
| % of control | 156 | 124 | 145 | 25 |
| Group II | | | | |
| Control | 2.3 | 0.23 | 0.43 | 0.04 |
| Chitosan solution 0.473 liter | 2.4 | 0.24 | 0.33 | 0.05 |
| % of control | 104 | 104 | 77 | 125 |

Application rate of chitosan solution is 0.473 liter per 45.36 kilograms of seed. Chitosan solution is 2% chitosan and 98% inert ingredients.

EXAMPLE 11

Wheat Seedling Test Data

Seedling Crown Diameter

Variety: VONA
Planted: 1 November 1984
Harvested: 5 January 1985
Location: Alva, Oklahoma

| Treatment | No. of samples | mean crown diameter (cm) | Statistical Deviation | % of control |
|---|---|---|---|---|
| Control | 15 | 5.347 | 1.147 | 100 |
| Chitosan 250 μg/g | 15 | 8.893 | 5.154 | 166 |

EXAMPLE 12

1984-85 Vona Wheat Yield
Date of harvest: 5 June 1985
Location: Alva, Oklahoma

| Treatment | No. of plots | kg hectare | Statistical Deviation | % of control |
|---|---|---|---|---|
| control | 6 | 2858.1 | 5.6 | 100 |
| Chitosan 250 μg/g | 6 | 3355.8 | 5.9 | 117 |

EXAMPLE 13

1983-84 TAM W-101 Wheat Yield
Date of harvest: 12 June 1984
Location: Alva, Oklahoma

| Treatment | No. of plots | kg hectare | Statistical Deviation | % of control |
|---|---|---|---|---|
| control | 6 | 3349.1 | 5.9 | 100 |
| Chitosan 250 μg/g | 6 | 3685.3 | 6.2 | 110 |

EXAMPLE 14

1985 Comparison of Yield for Chitosan vs. Benlate
Location: Whitlow Farm, Pullman, Washington

| | Kg/hectare | % of control |
|---|---|---|
| I. Hill - 81 | | |
| H$_2$O Control[a] | 4794.9 | — |
| Benlate Treated[b] | 3651.7 | 76 |
| 1000 μg/g + Benlate[c] | 3396.1 | 71 |
| 500 μg/g + Benlate[c] | 3961.0 | 83 |
| 250 μg/g + Benlate[c] | 4041.7 | 84 |
| 125 μg/g + Benlate[c] | 4176.2 | 87 |
| 62 μg/g + Benlate[c] | 3254.9 | 68 |
| 1000 μg/g[c] | 4088.8 | 85 |
| 500 μg/g[c] | 4673.9 | 97 |
| 250 μg/g[c] | 5756.6 | 120 |
| 125 μg/g[c] | 5427.1 | 113 |
| 62 μg/g[c] | 4922.7 | 103 |
| II. Daws | | |
| H$_2$O Control[c] | 2757.3 | — |
| Benlate[c] | 1667.8 | 60 |
| 1000 μg/g + Benlate[c] | 1943.5 | 70 |
| 500 μg/g + Benlate[c] | 1049.1 | 38 |
| 250 μg/g + Benlate[c] | 1499.7 | 54 |
| 1000 μg/g[c] | 2710.2 | 98 |
| 500 μg/g[c] | 3961.0 | 144 |
| 250 μg/g[c] | 3799.6 | 138 |

[a]Averaged over 6 reps 3.048 m × 0.356 m.
[b]Averaged over 8 reps 3.048 m × 0.356 m.
[c]Averaged over 2 reps 3.048 m × 0.356 m.

EXAMPLE 15

1982-83 Stephens Wheat Harvest Yield

| Treatment | kg/hectare | % of control |
|---|---|---|
| H$_2$O Control[a] | 6536.7 | — |
| Chitosan 500 μg/g[b] | 7081.4 | 108 |
| Chitosan 250 μg/g[b] | 6691.4 | 102 |
| Chitosan 125 μg/g[b] | 6395.5 | 98 |
| Chitosan 62 μg/g[b] | 6247.5 | 96 |

[a]Average of 7.62 m × 1.22 m replications.
[b]Average of 7.62 m × 1.22 m replications.

EXAMPLE 16

1984-85 Daws Wheat Harvest Yield
Location: Whitlow Farm, Pullman, Washington

| Treatment | kg/hectare | % of Control |
|---|---|---|
| H$_2$O Control | 3214.6 | — |
| 1000 μg/g | 3712.2 | 115 |
| 500 μg/g | 4008.1 | 125 |
| 250 μg/g | 3880.3 | 121 |

All values averaged over four 3.048 m × 0.356 m replications.

EXAMPLE 17

| 1984-85 Hill '81 Wheat Yield Location: Whitlow Farm, Pullman, Washington | | |
|---|---|---|
| Treatment | kg/hectare | % of Control |
| $H_2O$ Control[a] | 4129.2 | — |
| 1000 $\mu$g/g[b] | 3920.7 | 95 |
| 500 $\mu$g/g[b] | 4337.6 | 105 |
| 250 $\mu$g/g[b] | 4963.1 | 120 |
| 125 $\mu$g/g[b] | 4922.7 | 119 |
| 62 $\mu$g/g[b] | 4297.3 | 104 |

[a]Average of 50 3.048 m × 0.356 m replications.
[b]Average of 10 3.048 m × 0.356 m replications.

EXAMPLE 18

| 1985 Corret Spring Oat Yield Location: Whitlow Farm, Pullman, Washington | | |
|---|---|---|
| Treatment | kg/hectare | % of Control |
| $H_2O$ Control[a] | 1001.6 | — |
| 500 $\mu$g/g[b] | 876.4 | 87 |
| 250 $\mu$g/g[b] | 793.0 | 79 |
| 125 $\mu$g/g[b] | 1544.2 | 154 |
| 62 $\mu$g/g[b] | 667.8 | 67 |

[a]Average of 35 3.048 m × 0.356 m replications.
[b]Average of 7 3.048 m × 0.356 m replications.

EXAMPLE 19

| 1985-86 Boyer Barley Yield Location: Soil Conservation Service Field Station Pullman, Washington | | | |
|---|---|---|---|
| Treatment | No. of plots | kg hectare | % of control |
| $H_2O$ Control | 12 | 4718.6 | 100 |
| Chitosan solution 0.1183 liters/ 45.36 kg seed | 13 | 5884.2 | 125 |
| $H_2O$ control | 12 | 4920.3 | 100 |
| Chitosan solution 0.1479 liters/ 45.36 kg seed | 13 | 5839.4 | 119 |
| $H_2O$ Control | 10 | 4965.1 | 100 |
| Chitosan solution 0.1775 liters/ 45.36 kg seed | 11 | 7677.5 | 155 |
| $H_2O$ Control | 11 | 6881.7 | 100 |
| Chitosan solution 0.2366 liters/ 45.36 kg seed | 13 | 8013.7 | 116 |
| $H_2O$ Control | 12 | 6298.9 | 100 |
| Chitosan solution 0.2958 liters/ 45.36 kg seed | 13 | 7139.5 | 113 |

Plot size = 3.048 m × 0.357 m = 1.087 m².
Chitosan solution is 2% chitosan and 98% inert ingredients.

Having fully described the present invention, it will be apparent to those skilled in the art that modifications to the method described herein may be made without departing from the scope of the present invention. While the embodiments described involve wheat, oats, and barley the process is generally applicable to cereal crops. Only the wheat, oats, and barley embodimetns have been included for the sake of brevity. Therefore, the scope of this invention is not intended to be limited except as may be required by the lawful scope of the following claims.

I claim:

1. Cereal crop seed treated by applying chitosan in solution to the seed.

2. The product of claim 1 wherein said cereal crop is wheat.

3. The product of claim 1 wherein said cereal crop is barley.

4. The product of claim 1 wherein said cereal is rye.

5. The product of claim 1 wherein said cereal crop is oats.

6. The product of claim 1 wherein said cereal crop is rice.

7. The product of claim 1 wherein the cereal crop seed in treated with chitosan in solution in an amount between 60 $\mu$g/g seed and 1000 $\mu$g/g seed.

8. An aqueous composition comprising chitosan which has been dissolved in a dilute aqueous acid and then neutralized to a pH greater than 6.0 but less than 7.0 while avoiding localized changes to a pH higher than 7.0.

9. The composition of claim 8 wherein said chitosan is dissolved by treating wastes from shrimp, lobster, and crustacean seafood industries having 10-30% chitosan in said dilute acid.

10. The composition of claim 8 wherein the dilute aqueous acid is acetic acid, dilute hydrochloric acid, sulfuric acid, or formic acid.

11. The composition of claim 8 wherein the chitosan has been deacetylated to an extent exceeding 90%.

12. The composition of claim 8 which is neutralized to a pH greater than 6.0 but less than 7.0 by the use of NaOH.

13. The composition of claim 12 wherein the pH is between 6.0 and 6.5.

14. A method of preparing a chitosan solution comprising dissolving chitosan in a dilute aqueous acid solution and then adding a sufficient amount of a base to neutralize said solution to a pH greater than 6.0 but less than 7.0 while avoiding localized changes to a pH higher than 7.0.

15. The method of claim 14 wherein the pH is between 6.0 and 6.5.

16. The method of claim 14 wherein the base is NaOH.

17. The method of claim 15 wherein the base is NaOH.

18. The method of claim 14 wherein the dilute aqueous acid is acetic acid, dilute hydrochloric acid, sulfuric acid, or formic acid.

19. The method of claim 14 wherein the chitosan has been deacetylated to an extent exceeding 90%.

* * * * *